United States Patent [19]
Knifton et al.

[11] Patent Number: 5,488,179
[45] Date of Patent: Jan. 30, 1996

[54] DITERTIARY BUTYL PEROXIDE PREPARATION FROM TERTIARY BUTYL HYDROPEROXIDE

[75] Inventors: John F. Knifton; Edward T. Marquis, both of Austin; Pei-Shing E. Dai, Port Arthur, all of Tex.

[73] Assignee: Texaco Chemical Inc., White Plains, N.Y.

[21] Appl. No.: 401,108

[22] Filed: Mar. 8, 1995

[51] Int. Cl.$^6$ .................................................. C07C 409/16
[52] U.S. Cl. ............................................ 568/578; 568/558
[58] Field of Search ............................... 568/578, 558, 568/570

[56] References Cited

U.S. PATENT DOCUMENTS

| | | | |
|---|---|---|---|
| 3,474,151 | 10/1969 | Grane | 568/578 |
| 4,740,292 | 4/1988 | Chen et al. | 568/578 |
| 4,810,809 | 3/1989 | Sanderson et al. | 568/578 |
| 4,900,850 | 2/1990 | Sanderson et al. | 568/578 |
| 5,288,919 | 2/1994 | Faraj | 568/578 |
| 5,312,998 | 5/1994 | Liotta, Jr. et al. | 568/578 |
| 5,371,298 | 12/1994 | Pourreau et al. | 568/578 |
| 5,420,357 | 5/1995 | Faraj | 568/578 |

*Primary Examiner*—Werren B. Lone
*Attorney, Agent, or Firm*—James L. Bailey; Kenneth R. Priem; Cynthia L. Hunter

[57] ABSTRACT

Disclosed is a method of selective preparation of ditertiary butyl peroxide from tertiary butyl hydroperoxide and t-butanol which comprises reacting said tertiary butyl hydroperoxide and t-butanol over a Beta-zeolite catalyst under hydroperoxide conversion conditions.

6 Claims, No Drawings

DITERTIARY BUTYL PEROXIDE PREPARATION FROM TERTIARY BUTYL HYDROPEROXIDE

FIELD OF THE INVENTION

The invention is concerned with the generation of ditertiary butyl peroxide. More particularly the invention relates to the selective generation of di-t-butyl peroxide from t-butyl hydroperoxide (tBHP) plus t-butanol (tBA). Still more particularly, this invention relates to the selective generation of di-t-butyl peroxide from t-butyl hydroperoxide (tBHP) plus t-butanol (tBA) using an acidic Beta zeolite catalyst.

BACKGROUND OF THE INVENTION

It is known that ditertiary butyl peroxide is a minor constituent of the reaction product when tertiary butyl hydroperoxide is thermally or catalytically decomposed to form tertiary butyl alcohol. Ditertiary butyl peroxide is a valuable commercial product used, for example, as a high temperature free radical initiator in chemical reactions. U.S. Pat. Nos. 4,810,809 and 4,900,850, to Sanderson et al. disclose methods which can be used to recover purified ditertiary butyl peroxide from a reaction product formed by the thermal or catalytic decomposition of tertiary butyl hydroperoxide.

In "Organic Peroxides" edited by Daniel Swern (Wiley Interscience, a Division of John Wiley & Sons, New York), in Vol II, page 157, it is stated that the metal-ion-catalyzed decomposition of primary hydroperoxide yields mainly alcohols, aldehydes and carboxylic acids.

In U.S. Pat. No. 2,854,487, Quin discloses the hydrogenation of hydrocarbon peroxides in the presence of hydrogen and palladium on activated alumina to provide carbinols.

In U.S. Pat. No. 3,474,151 it is disclosed that tertiary butyl alcohol starts to dehydrate at 450° .F and to decompose at a "rapid rate" at temperatures above 475° F. It was disclosed that residual quantities of hydroperoxide contaminants present in tertiary butyl alcohol could be thermally decomposed by heating the contaminated tertiary butyl alcohol at a temperature of 375° F. to 475° F. for about 1 to 10 minutes.

In U.S. Pat. No. 4,294,999 there is disclosed a process wherein isobutane is oxidized in a pressured reactor in the presence of solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane, U.S. Pat. No. 3,474,151, by heating the tertiary butyl alcohol at 375° to 475° F. for about 1 to 10 minutes. Heating tertiary butyl alcohol containing small amounts of peroxides at high temperatures for even short periods of time to remove the peroxides produces undesirable products such as isobutylene.

In U.S. Pat. No. 4,551,553 to Taylor et al. there is disclosed a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

Sanderson et al. disclose the use of a variety of catalysts for the decomposition of tertiary butyl hydroperoxide in a series of U.S. patents, including a catalyst composed of unsupported nickel, copper, chromia and iron (U.S. Pat. No. 4,704,482), a catalyst composed of iron, copper, chromia and cobalt (U.S. Pat. No. 4,705,903), a catalyst composed of a base treated hydrogenation catalyst from Groups VIB or VIIIB of the Periodic Table (U.S. Pat. No. 4,742,179), a catalyst consisting essentially of nickel, copper, chromium and barium (U.S. Pat. No. 4,873,380), a catalyst composed of a metal phthalocyanine promoted with a rhenium compound (U.S. 4,910,349), a catalyst composed of a base promoted metal phthalocyanine compound, (U.S. Pat. No. 4,912,269), a catalyst composed of a soluble ruthenium compound promoted with a bidentate ligand (U.S. Pat. No. 4,912,033), a catalyst composed of a metal porphine such as iron (III) or manganese(III) promoted with an alkyl thiol or an amine, a catalyst composed of an imidazole promoted metal phthalocyanine compound (U.S. Pat. No. 4,912,266), (U.S. Pat. No. 4,922,034), a catalyst composed of a metal phthalocyanine promoted with a thiol and a free radical inhibitor (U.S. Pat. No. 4,922,035), a catalyst composed of a borate promoted metal phthalocyanine, (U.S. Pat. No. 4,922,036) or a catalyst composed of a soluble ruthenium compound and an iron compound such as an acetate, a borate, a bromide, a chloride, a 1,3-propanedionate, a 2-ethyl-hexanoate, an iodide, a nitrate, a 2,4-pentanedionate, a perchlorate or a sulfate (U.S. Pat. No. 5,025,113).

In U.S. Pat. No. 5,345,009, to Sanderson et al., there is disclosed the conjoint production of tertiary butyl alcohol and ditertiary butyl peroxide from tertiary butyl hydroperoxide.

In U.S. Pat. No. 5,288,919, there is disclosed a process for the preparation of dialkyl peroxide which comprises reacting an alcohol (ROH) or an olefin having the formula

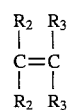

and mixtures in the liquid phase with a hydroperoxide ($R_1OOH$) in the presence of an inorganic heteropoly or isopoly acid catalyst.

A process is described in U.S. Pat. No. 5,312,998, where isobutane oxidate is reacted in the presence of a water soluble acid catalyst. A reaction mixture is formed which is separated into two phases, an aqueous phase and an organic phase which contains the ditertiary butyl peroxide which is subjected to a series of separation steps to recover the product.

It would be desirable if there were an improved method available for selectively generating ditertiary butyl peroxide which demonstrated improved yields of di-t-butyl peroxide and a simpler means of recovery, preferably through the use of a heterogeneous, solid acid catalyst.

SUMMARY OF THE INVENTION

In accordance with the foregoing the novel process of the instant invention for selectively generating di-t-butyl peroxide from t-butylhydroperoxide plus t-butanol comprises bringing said tertiary butyl hydroperoxide charge into contact with a solid acid decomposition catalyst comprising a Beta-zeolite.

DESCRIPTION OF THE INVENTION

The method of this invention for selective preparation of di-t-butyl peroxide by decomposition of t-butyl hydroperoxide plus t-butanol in the presence of acidic Beta zeolite catalysts can be represented by the following equation:

$$t\text{-}C_4H_9OOH + t\text{-}C_4H_9OH \rightarrow t\text{-}C_4H_9OOC_4H_9\text{-}t + H_2O \qquad (Eq.\ 1)$$

The tertiary butyl hydroperoxide charge stock may comprise an isobutane oxidation product wherein the tertiary butyl hydroperoxide is dissolved in a mixture of isobutane and tertiary butyl alcohol or may comprise an isobutane oxidation product enriched by the addition of tertiary butyl alcohol, such that the solution of tertiary butyl alcohol in the mixture of isobutane with tertiary butyl alcohol contains from about one to about 80 wt. % of tertiary butyl hydroperoxide.

Alternately, the isobutane reaction product may be charged to a distillation zone where unreacted isobutane is removed as a distillate fraction for recycle to thereby provide a solution of tertiary butyl hydroperoxide in tertiary butyl alcohol containing about one to about 80 wt % of tertiary butyl hydroperoxide.

The catalyst to be used in accordance with the instant invention as a hydroperoxide decomposition catalyst comprises a solid acidic catalyst in the form of an acidic Beta zeolite.

The acidic zeolite catalyst which is suitable for the instant invention is Beta zeolite. The composition of zeolite beta is described in U.S. Pat. Nos. 3,308,069; 4,419,220; 4,518,485 and 4,740,292. In those references, zeolite beta is typically described as follows:

Zeolite beta is a crystalline aluminosilicate having a pore size greater than 5 Angstroms. The composition of the zeolite, as described in U.S. Pat. No. 3,308,069, in its as synthesized form may be expressed as follows:

$$[XNa\ (1.0\pm0.1\text{-}X)\ TEA]AlO_2.YSiO_2.WH_2O$$

where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

In an article titled "The Framework Topology Of Zeolite Beta" published in ZEOLITES, 1988, Vol 8 1 November, 446–452, J. B. Higgins, et al. disclose what is known about the framework topology of zeolite beta. As discussed in the J. B. Higgins, et al. reference, the first clues to the crystal structure of zeolite beta were evidenced from chemical and physical property measurements, Ion-exchange isotherms of Na-β at 25° C. indicated that cations as large as tetraethylammonium (TEA$^+$) exchanged completely into the pore system. This behavior suggests that beta contains at least 12-membered rings opening into channels, because TEA$^+$ is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6–19.4 wt % and a measured density of 1.61 g/cm$^3$ ruled out undimensional pore systems such as those in ZSM-12, ZSM-22, ZSM-23 and ZSM-48. Structural similarities among beta, mordenite and ZSM-12 were suspected because all three may be synthesized in Na$^+$–TEA$^+$ systems from highly siliceous batch compositions. Further, zeolite beta is easily synthesized in the SiO$_2$/Al$_2$O$_3$ range of 30–50. This lies between TEA$^+$ mordenite (typically 10–30) and ZSM-12 (typically, >60), suggesting the beta framework contains large fractions of both 4- and 5-membered rings.

In an article by Tsai and Wang, "CUMENE DISPROPORTIONATION OVER ZEOLITE B.II. Stability Enhancement with Silica Deposition and Steam Pretreatment", Applied Catalysis, 77 (1991) 209–222, stability enhancement is discussed. Two methods, silica deposition and steam pretreatment, have been developed to substantially improve zeolite beta stability.

Ibid, p. 215, it is stated that zeolite beta has two types of three dimensional pore openings, the linear and the tortuous channel. The former has pore openings of 7.5 Å×5.7 Å and the latter has pore openings of 6.5 Å×5.6 Å. When silica, for example, is deposited on zeolite beta, the pore opening was narrowed or blocked by the deposited silica. It was concluded that silica deposition selectively removes strong acid sites and increases the population of medium acid sites.

In the fully base-exchanged form, zeolite beta has the composition:

$$[(X/n)M(1\pm0.1\text{-}X)H]AlO_2.YSiO_2.WH_2O$$

where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. No. 4,419,220.

Zeolite beta is characterized by the following X-ray diffraction pattern:

d Values of Reflection in zeolite beta
11.40±0.2
7.40±0.2
6.70±0.2
4.25±0.1
3.97±0.1
3.00±0.1
2.20±0.1

The preferred forms of zeolite beta are the highly acidic, high silica forms, having silica-to-alumina mole ratio of at least 10:1, and preferably in the range of 10:1 to 50:1 in the as-synthesized form, and a surface area of at least 100 m$^2$/g.

Suitable β-zeolites for the practice of this invention include Valfor C806β, Valfor CP815β and Valfor C861. Valfor® is the registered trademark of the PQ corporation. Valfor® C806β zeolite is zeolite beta powder in template cation form. It is a high silica shape selective zeolite which contains the organic template used in the crystallization step, having been isolated after filtration and washing of the synthesis product. C806β has a SiO$_2$/Al$_2$O$_3$ molar ratio of 23–26; the crystal size is 0.1–0.7 um; the surface area after calcination is about 700–750 m$^2$/g; the cyclohexane adsorption capacity after calcination is 19–24g/100g; Na$_2$O content is about 0.01–1.0% by weight anhydrous; and, the organic content is about 11–13% by weight, on a water-free basis.

Valfor® C815β zeolite is a calcined zeolite beta powder in hydrogen, sodium form. It is similar to C806β except the product has been calcined to decompose the organic template. C815β is a high silica, shape selective aluminosilicate with a large pore diameter. C815β also has a SiO$_2$/Al$_2$O$_3$ molar ratio of about 23–26; the crystal size, surface area, cyclohexane adsorption capacity and Na$_2$O are all within the same ranges as given for C806β.

Valfor® C861β is an extrudate made of 80% C815β powder and 20% alumina powder.

Said β-zeolites may optionally be modified with a halogen, a halogen-containing organic compound, or a halogen-containing acid. Said halogen may be fluorine, chlorine, bromine or iodine, but is preferably fluorine. In the case of fluoride treatment, the fluoride content of the treated β-zeolite may be in the range of 0.1 to 10 wt %, but preferably is about 1%. Said fluoride-treated zeolites may optionally be calcined, at temperatures of 200° C. and above, prior to further usage or modification.

Said catalysts may be formed in the presence of a binder, such as Group III or Group IV oxide. Group IV oxides used in conjunction with said β-zeolite include oxides of aluminum, silicon, titanium, zirconium, hafnium, germanium, tin and lead, as well as combinations thereof. Alumina is preferred. Said binders may comprise 10% to 90% of the formed catalyst.

The method of the instant invention may be conducted batchwise in kettles or by continuously passing the reactants through a tubular reactor.

The catalytic decomposition of tertiary butyl hydroperoxide is preferably conducted at a temperature within the range of about 20° to about 160° C. and, preferably, at a temperature within the range of about 60° to about 120° C. The reaction is preferably conducted at a pressure sufficient to keep the reactant and the reaction products in liquid phase. A pressure of about atmospheric to about 10,000 psi is desirable.

Flow rates of the charge solution to the reaction zone should be adjusted in order to provide an appropriate contact time within the reactor. In a batch process, the holding time may suitably be from about 0.1 to 100 hours, and preferably about 1 to 10 hours.

The t-butyl hydroperoxide may be a byproduct of the oxidation of isobutane, along with unreacted isobutane, tertiary butyl alcohol, and oxygen-containing by-products, which is then used as the charge stock of the instant invention. The concentration of tertiary butyl hydroperoxide in the charge stock can be one to 80 wt %.

As indicated, the catalytic decomposition of the tertiary butyl hydroperoxide may suitably be conducted at a temperature within the range of about 20° to about 160° C., preferably from about 60° to about 120° C., and most preferably from about 80° C. to 100° C. at autogenous pressure or, if desired, at a super atmospheric pressure up to 10,000 psig for a contact time within the range of about 0.1 to about 100 hours, preferably about 1 to 10 hours.

When the process is practiced in a continuous manner by continuously charging the tertiary butyl hydroperoxide charge stock to a reactor containing a fixed bed of pelleted hydroperoxide decomposition catalyst, the space velocity is suitably in the range of about 0.1 to about 10 volumes of tertiary butyl hydroperoxide charge stock per volume of catalyst per hour. Preferably, the space velocity is within the range of about 1 to about 2 volumes of tertiary butyl hydroperoxide charge stock per volume of catalyst per hour.

The following examples illustrate:

1. The generation of ditertiary butyl peroxide from tertiary butyl hydroperoxide using Beta zeolite (Example 1).
2. The preparation of ditertiary butyl peroxide using zeolite Beta as a 50:50 mix with alumina (Example 2).
3. The formation of ditertiary butyl peroxide via zeolite Beta catalysis over a range of synthesis conditions (Table 2), including changes in:

Operating Temperature
Hold Times
Molar Feed Ratios
Catalyst Initial Concentration.

EXAMPLE 1

This example illustrates the synthesis of di-t-butyl peroxide from t-butylhydroperoxide via zeolite Beta catalysis. To a 300 cc capacity, stainless steel batch reactor, fitted with temperature, pressure controls and a mechanical stirrer was charged 50 g of isobutane oxidate (50% t-butylhydroperoxide and 50% t-butanol), plus 50 g of t-butanol and 20 g of zeolite Beta (C861B, 80% zeolite Beta, 20% alumina binder, in powder form). The mixture was flushed with nitrogen, pressured to 50 psi with nitrogen, with stirring, then heated to 80° C., for 4 hours, with continued stirring technology.

Upon cooling, the recovered product mix was weighed (111 g), filtered to recover used zeolite catalyst, and the liquid filtrate analyzed by glc. and gc-ms.

| Typical product composition was as follows: | |
|---|---|
| t-Butanol | 65.5% |
| Di-t-butyl peroxide | 24.7% |
| t-Butylhydroperoxide | 3.5% |
| Isobutylene | 1.6% |

Estimated t-butylhydroperoxide conversion 86%

EXAMPLE 2

Following the procedures and using the equipment of Example 1, the subject synthesis was effected using a 50% Beta zeolite, 50% alumina mix.

The results of this synthesis are summarized in Table 1, where the abbreviations are: Isobutylene ($C_4H_8$), t-butanol (tBA), di-t-butylperoxide (DTBP) and t-butylhydroperoxide (TBHP).

TABLE I

| Di-t-Butylperoxide from t-Butylhydroperoxide | | | | | |
|---|---|---|---|---|---|
| | | Product Composition % | | | TBHP Conv. |
| Example | Catalyst | $C_4H_8$ | tBA | DTBP | TBHP | (%) |
| 2 | 50% Beta | 3.7 | 60.0 | 27.5 | 3.7 | 85 |

EXAMPLES 3–9

These Examples illustrate the effects of experimental variables upon the synthesis of di-t-butylperoxide using zeolite Beta as catalyst.

Following the procedures and using the equipment of Example 1, the reactor was charged with 50 g of isobutane oxidate (50% t-Butylhydroperoxide and 50% t-Butanol), plus 50 g of t-butanol and zeolite Beta (C861 β, 80% Beta, $SiO_2/Al_2O_3$ molar ratio of 23–26. The mixture was flushed with nitrogen, pressured to 50 psi with nitrogen, with stirring then heated to temperature with continuing stirring.

TABLE 2

Di-t-Butylperoxide from t-Butylhydroperoxide

| Example | Beta Zeolite (gms) | TEMP. (°C.) | Time (HRS) | Initial tBA/TBHP Mole Ratio | Product Composition (%) | | | | TBHP Conv. (%) |
|---|---|---|---|---|---|---|---|---|---|
| | | | | | $C_4H_8$ | tBA | DTBP | TBHP | |
| 3 | 20 | 80 | 2 | 3.65 | 4.0 | 65.8 | 19.1 | 5.4 | 78 |
| 4 | 20 | 80 | 8 | 3.65 | 2.1 | 64.7 | 23.9 | 1.0 | 96 |
| 5 | 20 | 60 | 4 | 3.65 | 0.9 | 72.3 | 9.7 | 14.9 | 40 |
| 6 | 20 | 100 | 4 | 3.65 | 6.0 | 49.7 | 21.1 | 0.3 | 99 |
| 7 | 10 | 80 | 4 | 3.65 | 4.2 | 64.9 | 19.0 | 7.1 | 72 |
| 8 | 5 | 80 | 4 | 3.65 | 2.9 | 67.4 | 14.2 | 12.4 | 50 |
| 9 | 20 | 80 | 4 | 6.09 | 1.8 | 74.1 | 15.9 | 3.1 | 81 |

What is claimed is:

1. A method for selectively generating ditertiary butyl peroxide which comprises bringing a solution of tertiary butyl hydroperoxide charge stock in tertiary butyl alcohol into contact with a catalytically effective amount of an acidic Beta zeolite catalyst in a reaction zone in a liquid phase under hydroperoxide conversion conditions including a temperature within the range of about 20° C. to 160° C. and a pressure of about ATM to 10,000 psig selectively generate ditertiary butyl peroxide, along with t-butanol, from tertiary butyl hydroperoxide, and recovering said ditertiary butyl peroxide product.

2. The method of claim 1 wherein the charge stock contains from one to 80 wt % tertiary butyl hydroperoxide and the conversion conditions include a temperature of from about 60° C. to 120° C.

3. The method of claim 1 wherein the space velocity in the reaction zone is in the range of about 0.1 to about 10 volumes of tertiary butyl hydroperoxide charge stock per volume of catalyst per hour.

4. The method of claim 1 wherein the β-zeolite catalyst has a silica:alumina molar ratio in the range of 10:1 to 500:1.

5. The method of claim 1 wherein the β-zeolite has a surface area, after calcination of at least 100 m²/g.

6. The method of claim 1 wherein the β-zeolite is formed in the presence of a binder selected from a Group III or Group IV oxide, wherein the binder comprises 10 to 90% of the formed catalyst.

* * * * *